United States Patent [19]

Bugaut et al.

[11] Patent Number: 4,563,188
[45] Date of Patent: Jan. 7, 1986

[54] PARA-PHENYLENEDIAMINES WHICH CAN BE USED IN OXIDATIVE HAIR DYEING

[75] Inventors: Andreé Bugaut, Boulogne-Billancourt; Patrick Andrillon, Aulnay-sous-Bois, both of France

[73] Assignee: L'Oreal, Paris, France

[21] Appl. No.: 27,383

[22] Filed: Apr. 5, 1979

[30] Foreign Application Priority Data

Apr. 6, 1978 [FR] France ................................ 78 10275

[51] Int. Cl.$^4$ ........................ A61K 7/12; C07C 143/74
[52] U.S. Cl. ......................................... 8/410; 424/47; 564/99
[58] Field of Search ...................... 8/10, 10.1, 10.2, 11, 8/410; 564/99

[56] References Cited

U.S. PATENT DOCUMENTS

| | | | |
|---|---|---|---|
| 4,094,635 | 6/1978 | Bugaut et al. | 8/10.1 X |
| 4,119,399 | 10/1978 | Feinland et al. | 8/10.1 X |
| 4,125,367 | 11/1978 | Bugaut et al. | 8/10.2 X |
| 4,259,261 | 3/1981 | Bugaut et al. | 564/99 |
| 4,268,264 | 5/1981 | Grollier et al. | 8/410 |
| 4,314,810 | 2/1982 | Fourcadier et al. | 8/410 |
| 4,401,663 | 8/1983 | Buckwalter et al. | 564/99 |
| 4,420,637 | 12/1983 | Bugaut et al. | 8/410 |

FOREIGN PATENT DOCUMENTS 2349325 11/1977 France .
1421600 1/1976 United Kingdom .

OTHER PUBLICATIONS

Hackh's Chem. Dict., 4th Edition, p. 250.

Primary Examiner—Ethel G. Love
Attorney, Agent, or Firm—Fleit, Jacobson, Cohn & Price

[57] ABSTRACT

New para-phenylenediamines suitable for use in the oxidative dyeing of hair are described which provide useful "background" green shades. These compounds have the formula:

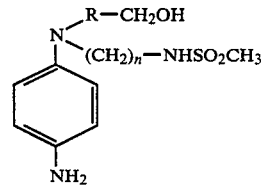

in which n is an integer from 2 to 6 and R denotes an unsubstituted or mono- or poly-hydroxy substituted linear or branched alkylene group containing up to 6 carbon atoms, which alkylene group can optionally contain one or more ether groups.

33 Claims, No Drawings

PARA-PHENYLENEDIAMINES WHICH CAN BE USED IN OXIDATIVE HAIR DYEING

DESCRIPTION

The present invention relates to para-phenylenediamines which can be used in so-called oxidative hair dyeing.

In so-called "oxidative hair dyeing", the use of para-phenylenediamines as dyestuff precursors is well known. After application to the hair in an oxidising alkaline medium, generally in the presence of hydrogen peroxide, and after penetration into the fibre, these para-phenylenediamines, which are colourless compounds commonly referred to as "oxidative bases", lead to the in situ formation of coloured compounds. The formation of these coloured compounds results either from the oxidative condensation of the para-phenylenediamines with themselves, or from the oxidative condensation of the para-phenylenediamines with meta-phenylenediamines, meta-diphenols or meta-aminophenols, that is to say with compounds commonly referred to as "couplers", which are generally present in dyeing compositions.

In order to be selected for so-called oxidative hair dyeing, the para-phenylenediamines must first satisfy two main criteria, namely, on the one hand, they must be very harmless, and, on the other hand, they must make it possible to impart to the hair, in an oxidising alkaline medium, colourations which are sufficiently resistant to light, adverse weather conditions, shampoos and perspiration.

However, in addition to these essential properties it is also important that these para-phenylenediamines can by themselves impart to the keratin fibres a dark so-called "background" colouration, without which it would be difficult for those skilled in the art to formulate compositions producing natural shades. Although the para-phenylenediamines which have generally been used hitherto make it possible, by themselves, to obtain "background" colourations in chestnut, brown, grey or black shades, the para-phenylenediamines of the present invention exhibit the exceptional advantage, whilst being perfectly harmless and producing colourations having a good stability, that they make it possible to obtain dark so-called "background" colourations in green shades which can range from bronze green, which is more or less reddish brown, to intense bottle green, depending on the nature of the carrier for the dyeing compositions in which they are present, the pH of these compositions and their concentration in these compositions. These dark green colourations exhibit very good stability to light, adverse weather conditions and washing. The addition of green to the hair dye formulation is highly desirable for obtaining dull shades, for "toning down" shades which are too warm or too red, and possibly for correcting the tendency of some dyes to become red with time.

The para-phenylenediamines of the present invention are represented by the general formula (I):

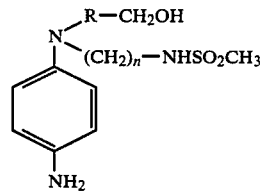

in which n is an integer from 2 to 6 and R is a linear or branched alkylene group containing 1 to 6 carbon atoms, which can optionally be mono- or poly-hydroxylic and can also contain ether groups and the invention includes their non-toxic salts with inorganic or organic acids, such as the hydrochlorides, sulphates, phosphates and tartrates, in anhydrous or hydrated form.

Amongst these compounds N,N-(β-hydroxyethyl-β-mesylaminoethyl)-para-phenylenediamine and its salts may be mentioned in particular.

The compounds of this invention can be prepared by a three-stage process from para-phenylenediamine which is monosubstituted on the nitrogen, this compound having the formula (II) and being isolated and stored in the form of a salt:

$$HN-(CH_2)_n-NHSO_2CH_3 \quad (II)$$
(with NH$_2$ on the ring)

n being an integer from 2 to 6, in accordance with the following typical reaction scheme:

(II) [ring with HN–(CH$_2$)$_n$–NHSO$_2$CH$_3$ and NH$_2$, .2HCl] $\xrightarrow[\text{reducing agent}]{\text{acetylation alkaline}}$ (III) [ring with HN–(CH$_2$)$_n$–NHSO$_2$CH$_3$ and NHCOCH$_3$] $\xrightarrow{XRCH_2OH}$ (IV) [ring with N(R–CH$_2$OH)(CH$_2$)$_n$–NHSO$_2$CH$_3$ and NHCOCH$_3$] $\xrightarrow{\text{acid hydrolysis}}$ -continued

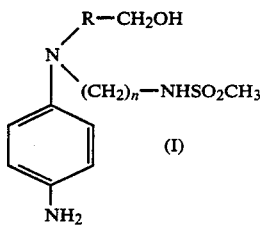

The first stage consists in selectively acetylating the primary amine group of the para-phenylenediamine (II), in water, preferably with the aid of acetic anhydride, after having liberated the para-phenylenediamine from its starting salt with the aid of an alkaline reducing agent, such as sodium sulphite, which protects the para-phenylenediamine (II) from any oxidation in the air before the monoacetylation is complete.

The second stage consists in substituting, by a group —RCH$_2$OH, the secondary amine group which has not been acetylated in the first stage, R having the above-mentioned meaning.

For this purpose, a halohydrin X—R—CH$_2$OH is condensed with the compound (III) obtained in the first stage, X being a halogen, preferably a bromine atom. The condensation is carried out in boiling water in the presence of an alkaline carbonate to capture or neutralise the acid liberated. After a heating time of the order of 4 to 24 hours, the reaction medium is desirably filtered and the filtrate cooled to, say, 0° C. in order to obtain the desired product in crystalline form. The crystalline product is filtered off and recrystallised, if necessary, from water or from an aqueous-alcoholic mixture.

The third stage consists in deacetylating the primary amine group which has been protected by acetylation in the first stage.

For this purpose, the compound (IV) obtained in the second stage is subjected to conventional acid hydrolysis by heating it, advantageously at about 100° C., in an aqueous solution of an acid, preferably in an aqueous solution of hydrochloric acid, of suitable concentration. The mixture is then conveniently evaporated to dryness in vacuo in order to obtain the compound (I) in the form of the salt.

The present invention also provides compositions suitable for dyeing keratin fibres especially human hair, which contain at least one compound of the formula (I) in an aqueous vehicle.

The compounds of the formula (I) are suitably used in the compositions of the invention at concentrations from 0.02 to 6%, and preferably from 0.15 to 5%, by weight, based on the total weight of the composition.

The compositions of the invention can also contain other oxidative dyestuff precursors.

They can contain, for example, other para-phenylenediamines such as: para-phenylenediamine, para-toluylenediamine, 2,6-dimethyl-para-phenylenediamine, 2,6-dimethyl-3-methoxy-para-phenylenediamine, N-(β-methoxyethyl)-para-phenylenediamine, 4-N-[β-(β'-hydroxyethoxy)-ethyl]-aminoaniline, 4-N,N-(β-hydroxyethyl)-aminoaniline, 4-(N-ethyl-N-carbamylmethyl)aminoaniline and also their salts.

They can also contain para-aminophenols, for example: para-aminophenol, 4-(N-methylamino)-phenol, 2-chloro-4-aminophenol, 3-chloro-4-aminophenol, 2-methyl-4-aminophenol and their salts.

They can also contain ortho-phenylenediamines and ortho-aminophenols, optionally possessing substituents on the nucleus or on the amine groups.

The dyeing compositions of the present invention generally contain, in combination with the compounds (I) and optionally with other para-phenylenediamines or with para-aminophenols, couplers which give, by oxidative coupling with the oxidative bases, indoanilines, indamines or indophenols of various shades, which contribute to modifying and enriching the sheen of the "background" colourations which are imparted to the hair by the products resulting from the condensation of the oxidative bases with themselves.

Couplers which may be mentioned are meta-diphenols, such as: resorcinol, 2-methylresorcinol and 5-methyl-resorcinol, meta-aminophenols, such as: meta-aminophenol, 2-methyl-5-aminophenol, 2-methyl-5-[N-(β-hydroxyethyl)amino]-phenol, 2-methyl-5-[N-(β-mesylaminoethyl)-amino]-phenol, 2,6-dimethyl-3-aminophenol, 6-hydroxybenzomorpholine and their salts, meta-phenylenediamines, such as: 2,4-diaminoanisole, 2,4-diaminophenoxyethanol, 6-aminobenzomorpholine, 2-N-(β-hydroxyethyl)-amino-4-aminophenoxyethanol and their salts, and meta-acylaminophenols, meta-ureidophenols and meta-carbalkoxyaminophenols, such as: 2-methyl-5-acetylaminophenol, 2,6-dimethyl-5-acetylaminophenol, 2-methyl-5-ureidophenol and 2-methyl-5-carbethoxyaminophenol.

The following may be mentioned as further couplers which can be used in the compositions of the invention: α-naphthol and the couplers possessing an active methylene group, such as β-ketone compounds and pyrazolones, and also their salts.

Further oxidative dyestuff precursors which can also be present in the compositions of the invention are leuco derivatives of indoanilines and/or of indophenols, for example: 4,4'-dihydroxy-2-amino-5-methyldiphenylamine, 2-amino-4-hydroxy-5-methyl-4'-N,N-(β-hydroxyethyl)-amino-diphenylamine and 2,4-dihydroxy-5-methyl-4'-N-(β-methoxyethyl)-aminodiphenylamine dihydrochloride.

Further precursors for hair colouring which can be present in the compositions are the precursors of the benzene series which contain at least three nuclear substituents of the hydroxy, methoxy and/or amino type, such as: 2,6-diaminohydroquinone dihydrochloride, 2,6-diamino-4-N,N-ethylaminophenol trihydrochloride, 2,4-diaminophenol dihydrochloride, 1,2,4-trihydroxybenzene, 2,3,5-trihydroxytoluene and 4-methoxy-2-amino-N-(β-hydroxyethyl)-aniline.

In order to shade and enrich with sheen the colourations imparted by the dyestuff precursors in an oxidising medium, there may be added to the compositions of the invention direct dyestuffs such as azo and anthraquinone dyestuffs and, more particularly, nitrobenzene derivatives, for example: 3-nitro-4-aminophenol, 3-nitro-4-N-(β-hydroxyethyl)-aminophenol, 2-methyl-5-amino-6-nitrophenol, 2-N-(β-hydroxyethyl)-amino-5-nitroanisole and 3-nitro-4-N'-methylamino-N,N-(β-hydroxyethyl)-aniline.

Hydroxynaphthoquinone compounds, such as juglone (5-hydroxy-1,4-naphthoquinone) or lawsone (2-hydroxy-1,4-naphthoquinone), can also be added to the compositions.

The colouring agents other than the compounds of the formula (I), that is to say the other para-phenylenediamines, the para-aminophenols, the ortho-phenylenediamines and ortho-aminophenols, the couplers, the other dyestuff precursors and the direct dyestuffs, which may be present in the compositions of the invention, are suitably present in an amount from 0.02 to 6% by weight, preferably from 0.1 to 3% by weight, based on the total weight of the composition.

The pH of the dyeing compositions of the invention is generally from 8 to 11, but is preferably from 9 to 11. It can be adjusted to the desired value with the aid of an alkalising agent such as ammonia, an alkaline carbonate or an alkanolamine such as mono-, di- or tri-ethanolamine.

The dyeing compositions according to the invention may also contain anionic, cationic, nonionic and/or amphoteric water-soluble surface-active agents. Amongst the surface-active agents which can be used, in particular, there may be mentioned alkylbenzenesulphonates, alkylnaphthalenesulphonates, sulphates, ether-sulphates and sulphonates of fatty alcohols, quaternary ammonium salts, such as trimethylcetylammonium bromide and cetylpyridinium bromide, ethanolamides of fatty acids, polyoxyethyleneated acids and alcohols, polyoxyethylenated alkylphenols and also polyoxyethylenated alkyl-sulphates. The surface-active agents are suitably present in the compositions according to the invention in an amount from 0.5 to 40% by weight, and preferably from 4 to 30% by weight, relative to the total weight of the composition.

Organic solvents can also be added to the compositions according to the invention in order to solubilise compounds which would not be sufficiently soluble in water. Amongst the solvents which can advantageously be used, there may be mentioned, by way of example, alkanols, such as ethanol and isopropanol, glycerol, glycol or glycol ethers, such as butylglycol, ethylene glycol, propylene glycol and diethylene glycol mono-ethyl ether and monomethyl ether, and mixtures thereof. The solvents are advantageously present in an amount from 1 to 40% by weight, and preferably from 5 to 30% by weight, relative to the total weight of the composition.

Thickening products which can be incorporated in the compositions according to the invention are advantageously sodium alginate, gum arabic, cellulose derivatives, such as methylcellulose, hydroxyethylcellulose, hydroxypropylcellulose, hydroxymethylcellulose and carboxymethylcellulose, or acrylic acid polymers; inorganic thickeners, such as bentonite, can also be used. The thickeners are preferably present in an amount from 0.5 to 5% by weight, and preferably from 0.5 to 3% by weight, relative to the total weight of the composition.

Antioxidants can also be added to the compositions according to the invention; preferred antioxidants include sodium sulphite, thioglycolic acid, sodium bisulphite, ascorbic acid and hydroquinone. These antioxidants are advantageously present in the composition in an amount from 0.05 to 1.5% by weight, relative to the total weight of the composition.

The compositions according to the invention can also contain various adjuvants which are usually employed in cosmetics, such as penetrating agents, sequestering agents, buffers and perfumes.

The dyeing compositions according to the invention can be in the form of liquids, creams or gels or in any other form which is suitable for dyeing keratin fibres. Moreover, they can be packaged in aerosols in the presence of a propellant.

The dyeing compositions of the invention which contain at least one oxidative dyestuff precursor of the formula (I) are used for dyeing keratin fibres, and in particular human hair, in accordance with a process which involves development by means of an oxidising agent.

This process generally consists in mixing, at the time of use, the dyeing composition with an oxidising solution in a sufficient amount to develop the expected colour, and then in applying the resulting mixture to the hair.

The oxidising solution contains oxidising agents such as hydrogen peroxide, urea peroxide or persalts such as ammonium persulphate. A hydrogen peroxide solution of 20 volumes strength is preferably used.

The oxidising solution can additionally contain a leuco derivative of indoaniline and/or of indophenol, such as those described above.

The resulting mixture is applied to the hair and left for, say, 10 to 40 minutes, preferably 15 to 30 minutes, after which the hair is rinsed, washed (with shampoo), rinsed again and dried.

The following Examples further illustrate the present invention.

EXAMPLE 1

Preparation of N,N-(β-hydroxyethyl-β-mesylamino-ethyl)-para-phenylenediamine dihydrochloride monohydrate.

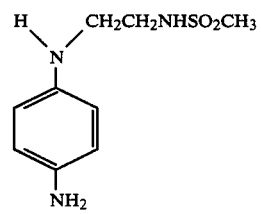

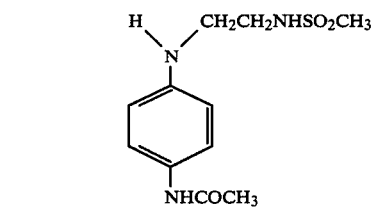

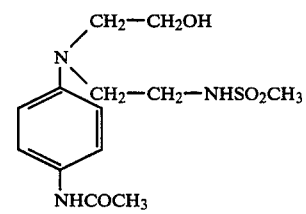

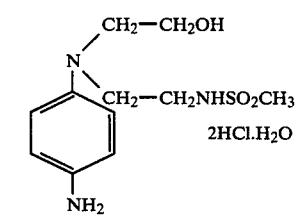

First stage:
Preparation of 4-acetylamino-N-(β-mesylaminoethyl)-aniline 0.2 mol (25.2 g) of sodium sulphite is added, at ambient temperature, to a solution of 0.1 mol (32.7 g) of N-(β-mexylaminoethyl)-para-phenylenediamine sulphate in 150 ml of water, and 0.13 mol (13.17 g) of acetic anhydride is introduced gradually, whilst stirring. When the addition is complete, stirring is continued for one hour and the resulting acetylated derivative which has precipitated in crystalline from is then dewatered (filted off). The product is dewatered, washed with water and dried in vacuo. After recrystallisation from alcohol and drying in vacuo, a product which melts at 130° C. is obtained.

| Analysis | % Calculated for $C_{11}H_{17}N_3SO_3$ | % Found |
|---|---|---|
| C % | 48.71 | 48.71 |
| H % | 6.27 | 6.15 |
| N % | 15.50 | 15.80 |
| S % | 11.81 | 12.01 |

Second stage:
Preparation of 4-acetylamino-N,N-(β-hydroxyethyl-β-mesylaminoethyl)-aniline 0.037 mol (10 g) of 4-acetylamino-N-(β-mesylaminoethyl)-aniline is dissolved in 31 ml of boiling water. 7.4 g of sodium carbonate and 0.148 mol (18.5 g) of glycol hydrobromide are added, whilst stirring. After stirring for 4 hours in a boiling water bath, the reaction medium is filtered and the filtrate is then left to stand for 48 hours at 0° C. The 4-acetylamino-N,N-(β-hydroxyethyl-β-mesylaminoethyl)-aniline which has precipitated in crystalline form is filtered off. After recrystallisation from boiling water and drying in vacuo, a product which melts at 118° C. is obtained.

| Analysis | % Calculated for $C_{13}H_{21}N_3SO_4$ | % Found |
|---|---|---|
| C % | 49.52 | 49.80 |
| H % | 6.67 | 6.77 |
| N % | 13.33 | 13.16 |
| S % | 10.16 | 10.36 |

Third stage:
Preparation of N,N-(β-hydroxyethyl-β-mesylaminoethyl)-para-phenylenediamine dihydrochloride monohydrate 0.0178 mol (5.6 g) of 4-acetylamino-N,N-(β-hydroxyethyl-β-mesylaminoethyl)-aniline in 12 ml of a 5N aqueous solution of hydrochloric acid is heated for thirty minutes in a boiling water bath. The water is then driven off in vacuo. After having kept the residue for two hours in vacuo at 60° C., a crystalline product is obtained which is chromatographically pure and which possesses the following characteristics:

| | |
|---|---|
| Molecular weight calculated for $C_{11}H_{19}N_3O_3S.2HCl.H_2O$ | 366 |
| Molecular weight obtained by potentiometric determination | 358 |

| Analysis | % Calculated for $C_{11}H_{19}N_3O_3S.2HCl.H_2O$ | % Found | |
|---|---|---|---|
| C % | 36.26 | 35.97 | 36.08 |
| H % | 6.31 | 6.40 | 6.44 |
| N % | 11.53 | 11.39 | 11.28 |
| Cl % | 19.50 | 19.54 | 19.66 |

EXAMPLE 2

The following dyeing composition is prepared:

| | |
|---|---|
| N,N—(β-hydroxyethyl-β-mesylaminoethyl)-para-phenylenediamine dihydrochloride monohydrate | 5 g |
| carboxymethylcellulose | 2 g |
| ammonium lauryl-sulphate | 5 g |
| ammonium acetate | 1 g |
| propylene glycol | 8 g |
| 35° B strength sodium bisulphite solution | 1 g |
| 22° B strength ammonia solution | 12 g |
| water q.s.p. | 100 g |

The pH of the composition is equal to 10.

100 grams of hydrogen peroxide of 20 volumes strength are added at the time of use.

When applied to bleached hair for 20 minutes at 25° C., this mixture imparts to the hair, after rinsing and shampooing, a *bronze green* colouration.

EXAMPLE 3

The following dyeing composition is prepared:

| | |
|---|---|
| N,N—(β-hydroxyethyl-β-mesylaminoethyl)-para-phenylenediamine dihydrochloride monohydrate | 5 g |
| oxyethyleneated oleyl alcohol containing 2 mols of ethylene oxide (per mol of alcohol) | 4.5 g |
| oxyethyleneated oleyl alcohol containing 4 mols of ethylene oxide | 4.5 g |
| ethanolamides of copra fatty acids | 10 g |
| hydroquinone | 0.1 g |
| 35° B strength sodium bisulphite solution | 1 g |
| sodium salt of diethylenetriaminepentaacetic acid | 2 g |
| propylene glycol | 4.5 g |
| butylglycol | 8 g |
| 96° strength ethanol | 8 g |
| 22° B strength ammonia solution | 10 g |
| water q.s.p. | 100 g |

The pH of the composition is equal to 10.

100 grams of hydrogen peroxide of 20 volumes strength are added at the time of use.

When applied to bleached hair for 25 minutes at 25° C., this mixture imparts to the hair, after rinsing and shampooing, a *bottle green* colouration.

EXAMPLE 4

The following dyeing composition is prepared:

| | |
|---|---|
| N,N—(β-hydroxyethyl-β-mesylaminoethyl)-para-phenylenediamine dihydrochloride monohydrate | 0.182 g |
| 2,4-diaminophenoxyethanol dihydrochloride | 0.12 g |
| oxyethyleneated oleyl alcohol containing 2 mols of ethylene oxide | 4.5 g |
| oxyethyleneated oleyl alcohol containing 4 mols of ethylene oxide | 4.5 g |
| ethanolamides of copra fatty acids | 10 g |
| hydroquinone | 0.1 g |
| 35° B strength sodium bisulphite solution | 1 g |
| sodium salt of diethylenetriaminepentaacetic acid | 2 g |

| | |
|---|---|
| -continued | |
| propylene glycol | 4.5 g |
| butylglycol | 8 g |
| 96° strength ethanol | 8 g |
| 22° B strength ammonia solution | 10 g |
| water q.s.p. | 100 g |

The pH of the composition is equal to 10.6.

100 grams of hydrogen peroxide of 20 volumes strength are added at the time of use.

When applied to 90% naturally white hair for 20 minutes at 25° C., this mixture imparts to the hair, after rinsing and shampooing, a *horizon blue* colouration.

EXAMPLE 5

The following dyeing composition is prepared:

| | |
|---|---|
| N,N—(β-hydroxyethyl-β-mesylaminoethyl)-para-phenylenediamine dihydrochloride monohydrate | 0.25 g |
| 2,6-dimethyl-5-acetylaminophenol | 0.12 g |
| butylglycol | 5 g |
| oxyethyleneated lauryl alcohol containing 10.5 mols of ethylene oxide | 5 g |
| 22° B strength ammonia solution | 10 g |
| water q.s.p. | 100 g |

The pH of the composition is equal to 10.6.

100 grams of hydrogen peroxide of 20 volumes strength are added at the time of use.

When applied to bleached hair for 25 minutes at 25° C., this mixture imparts to the hair, after rinsing and shampooing, a *forget-me-not* blue colouration.

EXAMPLE 6

The following dyeing composition is prepared:

| | |
|---|---|
| N,N—(β-hydroxyethyl-β-mesylaminoethyl)-para-phenylenediamine dihydrochloride monohydrate | 0.91 g |
| meta-aminophenol | 0.27 g |
| sodium lauryl-sulphate containing 19% of starting oxyethyleneated alcohol | 20 g |
| sodium salt of ethylenediaminetetraacetic acid | 0.2 g |
| 22° B strength ammonia solution | 10 g |
| 40% strength sodium bisulphite solution | 1 g |
| water q.s.p. | 100 g |

The pH of the composition is equal to 10.9.

100 grams of hydrogen peroxide of 20 volumes strength are added at the time of use.

When applied to 90% naturally white hair for 20 minutes at 22° C., this mixture imparts to the hair, after rinsing and shampooing, a *silvery mauve light grey* colouration.

EXAMPLE 7

The following dyeing composition is prepared:

| | |
|---|---|
| N,N—(β-hydroxyethyl-β-mesylaminoethyl)-para-phenylenediamine dihydrochloride monohydrate | 0.54 g |
| 2-methyl-5-N—(β-hydroxyethyl)-aminophenol | 0.25 g |
| sodium lauryl-sulphate containing 19% of starting oxyethyleneated alcohol | 20 g |
| sodium salt of ethylenediaminetetraacetic acid | 0.2 g |
| 22° B strength ammonia solution | 10 g |
| 40% strength sodium bisulphite solution | 1 g |
| water q.s.p. | 100 g |

The pH of the composition is equal to 10.9.

100 grams of hydrogen peroxide of 20 volumes strength are added at the time of use.

When applied to 90% naturally white hair for 25 minutes at 30° C., this mixture imparts to the hair, after rinsing and shampooing, a *pearlescent light beige* colouration *with a parma shade*.

EXAMPLE 8

The following dyeing composition is prepared:

| | |
|---|---|
| N,N—(β-hydroxyethyl-β-mesylaminoethyl)-para-phenylenediamine dihydrochloride monohydrate | 0.73 g |
| resorcinol | 0.22 g |
| sodium lauryl-sulphate containing 19% of starting oxyethyleneated alcohol | 20 g |
| sodium salt of ethylenediaminetetraacetic acid | 0.2 g |
| 22° B strength ammonia solution | 10 g |
| 40% strength sodium bisulphite solution | 1 g |
| water q.s.p. | 100 g |

The pH of the composition is equal to 10.8.

100 grams of hydrogen peroxide of 20 volumes strength are added at the time of use.

When applied to bleached hair for 20 minutes at 30° C., this mixture imparts to the hair, after rinsing and shampooing, a *pink pearlescent beige* colouration.

EXAMPLE 9

The following dyeing composition is prepared:

| | |
|---|---|
| N,N—(β-hydroxyethyl-β-mesylaminoethyl)-para-phenylenediamine dihydrochloride monohydrate | 0.57 g |
| para-aminophenol | 0.56 g |
| 2-methyl-5-aminophenol | 0.2 g |
| 2-methyl-5-carbethoxyaminophenol | 0.6 g |
| 3-nitro-4-N'—methylamino-N,N—(β-hydroxyethyl)-aniline | 1 g |
| oxyethyleneated oleyl alcohol containing 2 mols of ethylene oxide | 4.5 g |
| oxyethyleneated oleyl alcohol containing 4 mols of ethylene oxide | 9 g |
| propylene glycol | 9 g |
| 22° B strength ammonia solution | 5 g |
| 40% strength sodium bisulphite solution | 1 g |
| water q.s.p. | 100 g |

The pH of the composition is equal to 9.5.

70 grams of hydrogen peroxide of 20 volumes strength are added at the time of use.

This mixture is applied to 90% naturally white hair for 15 minutes at 25° C. After rinsing and shampooing, it imparts a *coppery light chestnut* colouration to this hair.

EXAMPLE 10

The following dyeing composition is prepared:

| | |
|---|---|
| N,N—(β-hydroxyethyl-β-mesylaminoethyl)-para-phenylenediamine dihydrochloride monohydrate | 2.6 g |
| o-aminophenol | 0.28 g |
| 2-methyl-5-amino-6-nitrophenol | 0.08 g |
| butylglycol | 5 g |
| oxyethyleneated lauryl alcohol containing 10.5 mols of ethylene oxide | 5 g |
| 40% strength sodium bisulphite solution | 0.5 g |
| 22° B strength ammonia solution | 5 g |

The pH of the composition is equal to 10.

100 grams of hydrogen peroxide of 20 volumes strength are added at the time of use.

When applied to bleached hair for 20 minutes at 25° C., this mixture imparts to the hair, after rinsing and shampooing, a *steel grey* colouration.

EXAMPLE 11

The following dyeing composition is prepared:

| | |
|---|---|
| N,N—(β-hydroxyethyl-β-mesylaminoethyl)-para-phenylenediamine dihydrochloride monohydrate | 2 g |
| 4-(N—ethyl-N—carbamylmethyl)-aminoaniline | 1.5 g |
| 2,4-diaminophenoxyethanol dihydrochloride | 0.1 g |
| 3-nitro-4-N—(β-hydroxyethyl)-aminophenol | 0.4 g |
| 1,2,4-trihydroxybenzene | 0.9 g |
| butylglycol | 5 g |
| oxyethyleneated lauryl alcohol containing 10.5 mols of ethylene oxide | 5 g |
| triethanolamine | 5 g |
| water q.s.p. | 100 g |

The pH of the composition is equal to 8.1

70 grams of hydrogen peroxide of 20 volumes strength are added at the time of use. When applied to bleached hair for 25 minutes at 25° C., this mixture imparts to the hair, after rinsing and shampooing, a *very dark brown* colouration.

EXAMPLE 12

The following dyeing composition is prepared:

| | |
|---|---|
| N,N—(β-hydroxyethyl-β-mesylaminoethyl)-para-phenylenediamine dihydrochloride monohydrate | 2 g |
| para-toluylenediamine dihydrochloride | 1 g |
| para-aminophenol | 0.78 g |
| 2-methyl-5-N—(β-hydroxyethyl)-aminophenol | 0.28 g |
| 2,6-dimethyl-5-acetylaminophenol | 0.6 g |
| meta-aminophenol | 0.03 g |
| sodium lauryl-sulphate containing 19% of starting oxyethyleneated alcohol | 20 g |
| sodium salt of ethylenediaminetetra-acetic acid | 0.2 g |
| 22° B strength ammonia solution | 10 g |
| 40% strength sodium bisulphite solution | 1 g |
| water q.s.p. | 100 g |

The pH of the composition is equal to 10.2.

100 grams of hydrogen peroxide of 20 volumes strength are added at the time of use.

When applied to 90% naturally white hair for 20 minutes at 25° C., this mixture imparts to the hair, after rinsing and shampooing, a *mahogany chestnut* colouration.

EXAMPLE 13

The following dyeing composition is prepared:

| | |
|---|---|
| N,N—(β-hydroxyethyl-β-mesylaminoethyl)-para-phenylenediamine dihydrochloride monohydrate | 3 g |
| para-phenylenediamine dihydrochloride | 1 g |
| para-aminophenol | 0.7 g |
| 2-methyl-5-N—(β-hydroxyethyl)-aminophenol | 0.3 g |
| 2,4-diaminophenoxyethanol dihydrochloride | 0.11 g |
| resorcinol | 0.04 g |
| 3-nitro-4-N—(β-hydroxyethyl)-aminophenol | 0.05 g |
| oxyethyleneated oleyl alcohol containing 2 mols of ethylene oxide | 4.5 g |
| oxyethyleneated oleyl alcohol containing 4 mols of ethylene oxide | 4.5 g |
| diethanolamides of copra fatty acids | 10 g |
| hydroquinone | 0.1 g |
| 35° B strength sodium bisulphite solution | 1 g |
| sodium salt of diethylenetriaminepenta-acetic acid | 2 g |
| propylene glycol | 4.5 g |
| butylglycol | 8 g |
| 96° strength ethanol | 8 g |
| 22° B strength ammonia solution | 10 g |
| water q.s.p. | 100 g |

The pH of the composition is equal to 10.

100 grams of hydrogen peroxide of 20 volumes strength are added at the time of use.

When applied to 95% naturally white hair for 25 minutes at 25° C., this mixture imparts to the hair, after rinsing and shampooing, a *coppery deep chestnut* colouration.

EXAMPLE 14

The following dyeing composition is prepared:

| | |
|---|---|
| N,N—(β-hydroxyethyl-β-mesylaminoethyl)-para-phenylenediamine dihydrochloride monohydrate | 2 g |
| 2,6-dimethyl-3-methoxy-para-phenylenediamine dihydrochloride | 0.3 g |
| 2,4-diaminophenoxyethanol dihydrochloride | 0.23 g |
| nonylphenol containing four mols of ethylene oxide (sold under the name "Remcopal 334" by Messrs. Gerland) | 15.2 g |
| nonylphenol containing nine mols of ethylene oxide (sold under the name "Remcopal 349" by Messrs. Gerland) | 15.2 g |
| propylene glycol | 15 g |
| 22° B strength ammonia solution | 5 g |
| water q.s.p. | 100 g |

The pH of the composition is equal to 9.8.

An oxidising solution containing 2 g of 4,4'-dihydroxy-5-methyl-2-aminodiphenylamine and 100 grams of hydrogen peroxide of 20 volumes strength is added at the time of use.

When applied to bleached hair for 20 minutes at 30° C., this mixture imparts to the hair, after rinsing and shampooing, a *grey* colouration *with a slight reddish brown sheen.*

EXAMPLE 15

The following dyeing composition is prepared:

| | |
|---|---|
| N,N—(β-hydroxyethyl-β-mesylaminoethyl)-para-phenylenediamine dihydrochloride monohydrate | 2 g |
| para-aminophenol | 0.2 g |
| 4-N—methylaminophenol sulphate | 0.2 g |
| 6-aminobenzomorpholine dihydrochloride | 0.2 g |
| 2-methylresorcinol | 0.3 g |
| 2-methyl-5-aminophenol | 0.08 g |
| 3-nitro-4-N—(β-hydroxyethyl)-aminophenol | 0.04 g |
| lawsone | 1 g |
| sodium lauryl-sulphate containing 19% of starting oxyethyleneated alcohol | 20 g |
| sodium salt of ethylenediaminetetraacetic acid | 0.2 g |
| triethanolamine | 6 g |
| 40% strength sodium bisulphite solution | 1 g |
| water q.s.p. | 100 g |

The pH of the composition is equal to 8.

60 grams of hydrogen peroxide of 20 volumes strength are added at the time of use.

When applied to bleached hair for 20 minutes at 25° C., this mixture imparts to the hair, after rinsing and shampooing, an *ashen light chestnut* colouration.

EXAMPLE 16

The following dyeing composition is prepared:

| | |
|---|---|
| N,N—(β-hydroxyethyl-β-mesylaminoethyl)-paraphenylenediamine dihydrochloride monohydrate | 2 g |
| para-aminophenol | 0.2 g |
| 4-N—methylaminophenol sulphate | 0.2 g |
| 6-aminobenzomorpholine dihydrochloride | 0.1 g |
| 2-methylresorcinol | 0.3 g |
| 2-methyl-5-aminophenol | 0.05 g |
| sodium lauryl-sulphate containing 19% of starting oxyethyleneated alcohol | 20 g |
| sodium salt of ethylenediaminetetraacetic acid | 0.2 g |
| triethanolamine | 4 g |
| 40% strength sodium bisulphite solution | 1 g |
| water q.s.p. | 100 g |

The pH of the composition is equal to 8.

100 grams of hydrogen peroxide of 20 volumes strength are added at the time of use.

When applied to bleached hair for 20 minutes at 25° C., this mixture imparts to the hair, after rinsing and shampooing, a *tin grey* colouration *with a pink sheen*.

We claim:

1. A compound having the general formula:

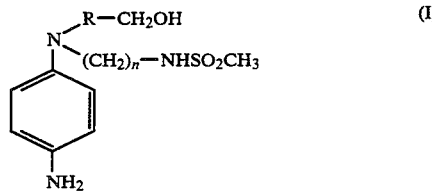

in which n is an integer from 2 to 6 and R denotes an unsubstituted or mono- or poly-hydroxy substituted linear or branched alkylene group containing up to 6 carbon atoms which alkylene group can optionally contain one or more ether groups, or an inorganic or organic acid addition salt thereof, the said compound or salt being anhydrous or hydrated.

2. A compound or salt according to claim 1, in which R is methylene and n is 2.

3. N,N-(β-Hydroxyethyl-β-mesylaminoethyl)-paraphenylenediamine dihydrochloride monohydrate.

4. A composition suitable for dyeing hair which comprises at least one compound of formula I as claimed in claim 1 in an aqueous vehicle.

5. Composition according to claim 4 in which the compound is N,N-(β-hydroxyethyl-β-mesylaminoethyl)-para-phenylenediamine dihydrochloride monohydrate.

6. Composition according to claim 4 which contains 0.02 to 6% by weight, based on the total weight of the composition of at least one compound of formula (I).

7. Composition according to claim 6 which contains 0.15 to 5% by weight, based on the total weight of the composition, of at least one compound of formula (I).

8. Composition according to claim 6 which also contains an oxidative dyestuff precursor other than a compound of formula (I), and/or a direct dyestuff, in an amount from 0.02 to 6%, by weight, based on the total weight of the composition.

9. Composition according to claim 8 which also contains a said oxidative dyestuff precursor and/or direct dyestuff in an amount from 0.1 to 3% by weight based on the total weight of the composition.

10. Composition according to claim 8 which contains at least one of para-phenylenediamine, para-toluylenediamine, 2,6-dimethyl-para-phenylenediamine, 2,6-dimethyl-3-methoxy-para-phenylenediamine, N-(β-methoxyethyl)-para-phenylenediamine, 4-N-[β-(β'-hydroxyethoxy)-ethyl]-aminoaniline, 4-N,N-(β-hydroxyethyl)-aminoaniline and 4-(N-ethyl-N-carbamylmethyl)-aminoaniline or a salt thereof.

11. Composition according to claim 8 which contains at least one of para-aminophenol, 4-N-methylaminophenol, 2-methyl-4-aminophenol, 2-chloro-4-aminophenol and 3-chloro-4-aminophenol or a salt thereof.

12. Composition according to claim 8 which contains at least one coupler which is a metadiphenol, meta-phenylenediamine, meta-aminophenol, meta-acylaminophenol, meta-ureidophenol, meta-carbalkoxyaminophenol, α-naphthol or a coupler containing an active methylene group.

13. Composition according to claim 12 in which the coupler is resorcinol, 2-methylresorcinol or 5-methylresorcinol, 2,4-diaminoanisole, 2,4-diaminophenoxyethanol, 2-N-(β-hydroxyethyl)-amino-4-aminophenoxyethanol, 6-aminobenzomorpholine or a salt thereof, metaaminophenol, 2-methyl-5-aminophenol, 2,6-dimethyl-3-aminophenol, 2-methyl-5-N-(β-hydroxyethyl)-aminophenol, 2-methyl-5-N-(β-mesylaminoethyl)-aminophenol, 6-hydroxybenzomorpholine or a salt thereof, 2-methyl-5-acetylaminophenol or 2,6-dimethyl-5-acetylaminophenol, 2-methyl-5-ureidophenol; 2-methyl-5-carbethoxyaminophenol, α-naphthol, a pyrazolone or a β-ketone compound, or a salt thereof.

14. Composition according to claim 8 which contains at least one leuco derivative of indoaniline and/or of indophenol.

15. Composition according to claim 14 which contains 4,4'-dihydroxy-2-amino-5-methyldiphenylamine, 2-amino-4-hydroxy-5-methyl-4'-N,N-(β-hydroxyethyl)-aminodiphenylamine or 2,4-dihydroxy-5-methyl-4'-N-(β-methoxyethyl)-aminodiphenylamine dihydrochloride.

16. Composition according to claim 8 which contains at least one oxidative dyestuff precursor which is a compound of the benzene series which contains at least three nuclear hydroxy, amino and/or methoxy substituents.

17. Composition according to claim 16 which contains 2,6-diaminohydroquinone dihydrochloride, 2,6-diamino-4-N,N-ethylaminophenol trihydrochloride, 2,4-diaminophenol dihydrochloride, 1,2,4-trihydroxybenzene, 2,3,5-trihydroxytoluene or 4-methoxy-2-amino-N-(β-hydroxyethyl)-aniline.

18. Composition according to claim 8 which contains at least one azo, anthraquinone and/or nitrobenzene direct dyestuff.

19. Composition according to claim 18 which contains 3-nitro-4-N-(β-hydroxyethyl)-aminophenol, 2-N-(β-hydroxyethyl)-amino-5-nitroanisole, 3-nitro-4-aminophenol, 3-nitro-4-N'-methylamino-N,N-(β-hydroxyethyl)-aniline or 2-methyl-5-amino-6-nitrophenol.

20. Composition according to claim 8, which contains 2-hydroxy-1,4-naphthoquinone and 5-hydroxy-1,4-naphthoquinone.

21. Composition according to claim 8 which has a pH from 8 to 11.

22. Composition according to claim 21 which has a pH from 9 to 11.

23. Composition according to claim 21, which contains an alkaline carbonate, or an alkanolamine.

24. Composition according to claim 4 which contains an anionic, cationic, nonionic and/or amphoteric water-soluble surface-active agent in an amount from 0.5 to 40% by weight, based on the total weight of the composition.

25. Composition according to claim 24 which contains 4 to 30% by weight based on the total weight of the composition of said surface-active agent.

26. Composition according to claim 4, which contains an organic solvent in an amount from 1 to 40% by weight based on the total weight of the composition.

27. Composition according to claim 26 which contains an alkanol, glycerol, glycol or glycol ether, or a mixture thereof, in an amount from 5 to 30% by weight based on the total weight of the composition.

28. Composition according to claim 4 which contains a thickener in an amount from 0.5 to 5% by weight and/or an antioxidant in an amount from 0.05 to 1.5% by weight, and/or penetrating agents, sequestering agents, buffers or perfumes.

29. Composition according to claim 28 which contains 0.5 to 3% by weight of thickener.

30. Composition according to claim 4 which is in the form of a liquid, cream, gel or aerosol.

31. Composition according to claim 4 which is suitable for dyeing human hair.

32. Process for dyeing hair which comprises mixing, at the time of use, a dyeing composition, as defined in claim 4 with an oxidising solution, applying the resulting mixture to the hair, and then rinsing, washing, rinsing again and drying the hair.

33. A compound or salt according to claim 1, in which the alkylene group contains one or more oxygen atoms interposed between two carbon atoms in the molecular structure.

* * * * *